(12) United States Patent
Kroll

(10) Patent No.: US 6,288,149 B1
(45) Date of Patent: Sep. 11, 2001

(54) HOT MELT ADHESIVE COMPOSITION INCLUDING SURFACTANT

(75) Inventor: Mark S. Kroll, Arden Hills, MN (US)

(73) Assignee: H. B. Fuller Licensing & Financing, Inc., St. Paul, MN (US)

( * ) Notice: Subject to any disclaimer, the term of this patent is extended or adjusted under 35 U.S.C. 154(b) by 0 days.

(21) Appl. No.: 09/415,430

(22) Filed: Oct. 8, 1999

Related U.S. Application Data

(60) Provisional application No. 60/103,675, filed on Oct. 9, 1998.

(51) Int. Cl.$^7$ ................................ C08K 5/13; C08K 5/05
(52) U.S. Cl. ............................ 524/81; 524/292; 524/306; 524/394; 524/396
(58) Field of Search ............................... 524/81, 292, 306, 524/394, 396

(56) References Cited

U.S. PATENT DOCUMENTS

| | | | |
|---|---|---|---|
| 5,120,765 | 6/1992 | Southwick et al. | 524/505 |
| 5,322,876 | 6/1994 | Sasaki et al. | 524/366 |
| 5,685,758 | 11/1997 | Paul et al. | 442/411 |
| 5,705,551 | 1/1998 | Sasaki et al. | 524/366 |

FOREIGN PATENT DOCUMENTS

| | | |
|---|---|---|
| 17796/97 | * 10/1997 | (AU) . |
| 0 888 786 A2 | 1/1999 | (EP) . |
| 8092075 | 4/1996 | (JP) . |

OTHER PUBLICATIONS

"Surfactant Blends for Modifying Polymers", 3M Company, by T. Klun, J. Temperante, A.J. Gasper, H. Johnson, & D. Weil ; Nonwovens World, Summer 1998, pp. 57–63.

\* cited by examiner

Primary Examiner—David W. Wu
Assistant Examiner—R. Harlan
(74) Attorney, Agent, or Firm—Nancy Quan

(57) ABSTRACT

Adhesive compositions are disclosed that include a block copolymer that includes monomers selected from the group consisting of styrene, isoprene, butadiene, and combinations thereof, from about 0.5% to about 10% by weight surfactant, and a tackifying agent. The adhesive composition has a surface tension of at least about 34 dynes/cm$^2$.

13 Claims, No Drawings

HOT MELT ADHESIVE COMPOSITION INCLUDING SURFACTANT

This application claims domestic priority to U.S. provisional application No. 60/103,675 filed Oct. 9, 1998.

BACKGROUND OF THE INVENTION

The invention relates to increasing surface tension.

Hot melt adhesive compositions are used in a variety of applications and on a variety of substrates including nonwoven webs, including tissue. Nonwoven webs are used commercially in a variety of applications including insulation, packaging, household wipes, surgical drapes, medical dressings, and disposable articles, e.g., diapers, adult incontinent products and sanitary napkins.

When hot melt adhesives are applied to nonwoven webs it is desirable that the adhesive possess good flexibility (i.e., hand) and be free from bleed through. When used in applications such as disposable diapers, sanitary napkins and bed pad constructions, it is also desirable for the hot melt adhesive to be capable of transmitting liquid or moisture from the nonwoven fibers into the superabsorbent or fluff core substrates that are common in such applications. This property is known as wicking and is used to draw moisture away from the body and into the adsorbent core as quickly as possible after the nonwoven is wetted. Some hot melt adhesives are hydrophobic and repel moisture, rather than drawing moisture through the adhesive layer.

SUMMARY

In one aspect, the invention features an adhesive composition that includes: a) a block copolymer comprising monomers selected from the group consisting of styrene isoprene, butadiene, and combinations thereof, b) from about 0.5% to about 10% by weight surfactant, and a tackifying agent. The adhesive composition has a surface tension of at least about 34 dynes/cm$^2$. In one embodiment, the block copolymer is styrene-isoprene-styrene.

In another embodiment, the surfactant is nonionic. In some embodiments, the surfactant is selected from the group consisting of fatty acid esters. The surfactant can be glycerol monostearate.

In one embodiment, the composition includes from about 10% by weight to about 80% by weight of the polymer, from about 0.5% by weight to about 10% by weight of the surfactant, and from about 20% by weight to about 50% by weight of the tackifying agent.

In some embodiments, the composition further includes a plasticizer. In one embodiment, the plasticizer includes a crystallizing plasticizer.

In another aspect, the invention features an article that includes a nonwoven substrate and an adhesive composition disposed on the substrate, where the adhesive composition has a surface tension of at least about 34 dynes/cm$^2$.

In other aspects, the invention features an article that includes adhesive fibers that include an above-described adhesive composition.

The adhesive composition provides a durable bond to a nonwoven article, including tissue articles, and exhibits flexibility, non-staining, and a viscosity sufficient to enable mass production. The adhesive also possesses exceptional thermal stability relative to moisture sensitive hot melt adhesive compositions. The hydrophilic nature of the adhesive composition facilitates transmission of fluids throughout nonwoven and porous articles that include the adhesive composition.

Other features of the invention will be apparent from the following description of preferred embodiments thereof, and from the claims.

DETAILED DESCRIPTION

The hot melt adhesive composition exhibits a surface tension of at least about 34 dynes/cm$^2$, more preferably at least about 40 dynes/cm$^2$, most preferably at least about 44 dynes/cm$^2$. The adhesive composition, when present on substrate or incorporated in a substrate, provides an increase in the surface tension of the substrate such that the substrate can be more easily wet by a fluid, e.g., water, body fluid (e.g., blood, urine, and combinations thereof) and combinations thereof (i.e., the adhesive improves the wettability of the substrate). The adhesive composition includes a polymer and a surfactant.

The polymer of the composition can be a block copolymer, an olefin-containing polymer, or a combination thereof. Preferably the polymer is a block copolymer.

A wide variety of block copolymers are useful in the hot melt adhesive of the resent invention including A-B-A triblock polymers, A-B diblock structures, star block copolymers, (A-B)$_n$ radial block copolymer, comb polymers, as well as branched and grafted versions of such, wherein the A endblock is a non-elastomeric polymer block, typically comprising polystyrene and/or vinyl, and the B block is an unsaturated conjugated diene or hydrogenated version thereof. In general, the B block is typically isoprene, butadiene, ethylene/butylene (hydrogenated butadiene), ethylene/propylene (hydrogenated isoprene), and mixtures thereof.

In general, block copolymers range in A block (styrene or vinyl) content from 0, as in the case of multi-arm (EP)n$^8$ 100% diblock polymers to about 50 wt-%. Typically, the non-elastomeric A block concentration ranges from about 10 wt-% to about 45 wt-% with respect to the weight of the block copolymer. Block copolymers also range in diblock contents from 0, wherein the block copolymer is 100% coupled, to 100% diblock, as previously mentioned. Further, the molecular weight of block copolymer is related to the solution viscosity at 77° F. (25° C.) of a given weight of polymer in toluene. The amount of block copolymer employed for determining the solution viscosity depends on the molecular weight. For relatively high molecular weight block copolymers, the solution viscosity is typically expressed as a function of a 10 wt-% block copolymer solution, whereas for more conventional and lower molecular weight block copolymers, a 25 wt-% block copolymer solution is employed. A preferred high molecular weight block copolymer is a substantially saturated A-B-A block copolymer, wherein the A block is polystyrene or vinyl and the B block is ethylene-butylene, ethylene-propylene or mixtures thereof, such as Kraton™ G-1651.

Useful commercially available polymers include, e.g., Kraton® D and G series block copolymers, available from Shell Chemical Company (Houston, Tex.), Europrene® Sol T block copolymers, e.g., SIS and SBS block copolymers, available from EniChem (Houston, Tex., Vector® block copolymers, e.g., SIS and SBS block copolymers, available from Exxon (Dexco) (Houston, Tex.), as well as others. Branched versions such as Kraton® TKG-101 having a styrene-ethylene/butylene-styrene backbone with isoprene side chains as well Kraton® G-1730, an S-EP-S-EP block copolymer having a terminal ethylene-propylene block rather than terminal polystyrene, are also useful for increasing tack.

Preferably the block copolymer is present in the adhesive composition in an amount of from about 10% by weight to about 50% by weight, more preferably from about 15% by weight to about 40% by weight.

Suitable olefin-containing polymers are those in which ethylene is polymerized with 15 to 45% by weight of copolymerizable monomers such as vinyl acetate, N-butyl acrylate, propylene, methyl acrylate, methyl acrylic acid, acrylic acid, metallocene catalyzed ethylene based polymers and the like, as well as any mixtures thereof.

Additional suitable polymers are pure homopolymers or copolymers of the following monomers: olefins, such as ethylene, propylene, butene, hexene octene, or other alpha-olefins; vinyl monomers, such as vinyl acetate, vinyl propionate, vinyl butyrate, vinyl hexanoate; acrylic monomers, such as acrylic acid and methacrylic acid, methacrylic acid esters, hydroxy ethyl acrylate, and the like. Preferred polymers are ethylene/vinyl acetate copolymers such as those obtainable from Dupont under the Elvax tradename. The preferred range for the vinyl acetate will be in the range of 18%–40% by weight, with 33% most preferred.

Other adhesive compositions may be prepared according to the invention using, as a base polymer, amorphous polyolefins or blends thereof. Amorphous polyolefins are made by the atactic polymerization of polypropylene. Polymerization occurs in the presence of a catalyst comprising a coordination complex of a transition metal halide with an organometallic compound. The solid amorphous polypropylene has a softening point of about 150° C. and a Brookfield viscosity at 190° C. of 1,000 to 50,000 cps. Suitable commercial products include Eastman Chemical's P 1010. Copolymers of amorphous polypropylene and ethylene (APE), or butene (APB), or hexene (APH), are suitable as a base polymer, as are terpolymers of propylene, butene and ethylene (APBE). Suitable commercially available products include those sold under the tradenames: Rextac 2315 from Rexene (APE); Rextac 2730 from Rexene (APB); Vestoplast 750 and 708 from Huls (APBE).

Blends of any of the above base materials, such as blends of ethylene vinyl acetate and atactic polypropylene may also be used to prepare the hot melt adhesive compositions.

The adhesive composition also includes a surfactant that is capable of increasing the surface tension of a surfactant free hot melt adhesive composition. The surfactant is sufficiently compatible with the polymer such that a useful hot melt adhesive composition is provided. The surfactant, when added in sufficient amount to the adhesive composition, imparts improved wicking properties to the adhesive. Preferably the adhesive properties of the adhesive composition are maintained upon the addition of the surfactant.

Suitable surfactants include nonionic, anionic, and cationic surfactants. Preferably the surfactant is nonionic. Examples of useful surfactants include glycerol monostearate, fatty acid esters and combinations thereof. Useful surfactants are also available commercially under the trade designations Atmer 685 and Atmer 100 fatty acid esters both available from ICI Americas, Emerest 2400 glycerol monostearate available from Emergy Group of Henkel Corp. (Cincinnati, Ohio), and combinations thereof.

Suitable silicone surfactants include ethoxylates or propoxylates of polydimethyl siloxane, having a number average molecular weight of 500 to 10,000, preferably 600 to 6000, such as are sold under the tradenames Silwet L-77, L-7605, and L-7500 available from OSi Specialties, Danbury, Conn.; and Product 193 from Dow Corning.

Exemplary nonionic surfactants include ethoxylates of (i) C sub 1–C sub 18, preferred C sub 8–C sub 9 alkyl or dialkyl phenols, such as those sold under the tradenames Macol DNP-10, available from PPG Industries, Gurnee, Ill., a 10 mole ethoxylate of dinonyl phenol, and Triton X-100, available from Union Carbide, a 10 mole ethoxylate of octyl phenol; (ii) alkyl C sub 8–C sub 60 mono-alcohols, such as those sold under the tradenames Surfonic L-12-8, an 8 mole ethoxylate of dodecanol, available from Huntsman Chemical Co., and Unithox 480, a 38 mole ethoxylate crystalline surfactant available from Petrolite Specialty Polymers Group, Tulsa, Okla.; and (iii) propylene oxide polymers, such as those sold under the tradename Pluronic, which are ethylene oxide/propylene oxide block copolymers having a Mn of 200 to 3000 available from BASF; and benzoates formed by partial condensation of benzoic acid with hydrophilic di or mono-ols having less than 1000 Mn, such as the product of condensing about three equivalents of benzoic acid with four equivalent of diethylene glycol, commercially available as XP 1010 from Velsicol Chemical. A preferred nonionic surfactant blend is Atmer 685, available from ICI Surfactants (Wilmington, Del.).

Suitable anionic surfactants are: C sub 8–C sub 60 alkyl ethoxylate sulfonates, (CH sub 3—(CH sub 2) sub 11-14—(O—CH sub 2 CH sub 2) sub 3—SO sub 3—Na sup +, such as, Avenel S30, available from PPG Industries; alkyl C sub 8–C sub 60 sulfonates, such as, Rhodapon UB (C sub 12—SO sub 3 sup–Na sup+) available from Rhone Poulenc; and alkyl/aromatic sulfonates, such as those sold under the tradename Calsoft.

Preferably the surfactant is present in the adhesive composition in an amount of 0.5% by weight to 10% by weight, more preferably from about 0.5% by weight to about 5% by weight, more preferably from about 1% by weight to about 4% by weight.

The adhesive can also include tackifying agent. The tackifying agents useful in the adhesive composition include, e.g., any compatible hydrocarbon resin, synthetic polyterpene, rosin esters, natural terpenes, and the like. More particularly, and depending upon the particular base polymer, the useful tackifying resins include (1) natural and modified rosins, for example, gum rosin, wood rosin, tall oil rosin, distilled rosin, hydrogenated rosin, dimerized rosin, and polymerized rosin; (2) glycerol and pentaerythritol esters of natural and modified rosins, for example, the glycerol ester of pale wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, for example, styrene/terpene and alpha methyl styrene/terpene; (4) polyterpene resins having a softening point, as determined by ASTM method E28-58T, of 80 degree(s) to 150 degree(s) C.; the latter polyterpene resins generally resulting from the polymerization of terpene hydrocarbons, such as the bicyclic monoterpene known as pinene, in the presence of Friedel-Crafts catalysts at moderately low temperatures; and hydrogenated polyterpene resins; (5) phenolic modified terpene resins and hydrogenated derivatives thereof, for example, the resin product resulting from the condensation, in an acidic medium, of a bicyclic terpene and a phenol; (6) aliphatic petroleum hydrocarbon resins having a Ball and Ring softening point of 70 degree(s) to 135 degree(s) C.; the latter resins resulting from the polymerization of monomers primarily consisting of olefins and di-olefins; and the hydrogenated aliphatic petroleum hydrocarbon resins; (7) aromatic petroleum hydrocarbon resins and the hydrogenated derivatives thereof; (8) alicyclic petroleum hydrocarbon resins and the hydrogenated derivatives thereof; (9) aromatic/aliphatic or alicyclic hydrocarbon resins such as those sold under the trademarks ECR 149B and ECR 179A by Exxon Chemical Company; and combinations thereof Examples of useful commercially available tackifying agents include Escorez 2596 $C_5$ aliphatic resins and Escorez 5600 aromatic dicyclopentadiene resins, which are available from Exxon Chemical, Zonatac 105LT styrenated terpene tackifying resins available from Arizona Chemical, and Eastotac H-130R aliphatic tackifying resins available from Eastman Chemical.

The adhesive composition preferably includes a tackifying agent in an amount sufficient to provide the necessary tack for the application. Preferably the tackifying agent is present in the composition in an amount of from 20% by weight to about 80% by weight, more preferably from about 40% by weight to about 60% by weight.

Various plasticizing or extending oils may also be present in the composition. The plasticizing or extending oils can be added to provide improved wetting action, viscosity control, and combinations thereof. The above broadly includes not only the usual plasticizing oils but also use of olefin oligomers and low molecular weight polymers, as well as vegetable and animal oils and their derivatives. Petroleum derived oils that may be employed are relatively high boiling materials containing only a minor proportion of aromatic hydrocarbons (preferably less than 30% and, more particularly, less than 15% by weight of the oil). Alternatively, the oil may be totally non-aromatic. The oligomers may be polypropylenes, polybutenes, hydrogenated polyisoprene, hydrogenated polybutadiene, and combinations thereof, having average molecular weights between about 350 and about 10,000.

Vegetable and animal oils include glycerol esters of the usual fatty acids and polymerization products thereof.

Also useful as plasticizers are polar synthetic compounds, such as the aliphatic and aromatic polyester plasticizers available from C. P. Hall Co., Stow, Ohio. Amides phosphate esters, sulfonamides, phthalates, and benzoates are also suitable at varying levels.

Preferred plasticizers include crystallizing plasticizers including, e.g., Benzoflex 352 (1,4-cyclohexanedimethanl dibenzoate, dicyclohexyl phthalate, Benzoflex S404 1,2,3-propane trioltribenzoate, and Benzoflex S552 1,3-propanediol, 2,2-bis[(benzoyloxy)methyl], dibenzoate.

The plasticizing agent can be present in the composition in amounts of up to about 20%, preferably from 0 to 15%, by weight.

Various petroleum derived waxes may also be used in amounts less than about 25% by weight of the composition in order to impart fluidity in the molten condition of the adhesive and flexibility to the set adhesive, and to serve as a wetting agent for bonding cellulosic fibers. The term 'petroleum derived wax' includes both paraffin and microcrystalline waxes having melting points within the range of 130° F. to 225° F. as well as synthetic waxes such as low molecular weight polyethylene or Fisher-Tropsch waxes.

An antioxidant or stabilizer may also be included in the adhesive compositions in amounts of up to about 3% by weight. Among the applicable antioxidants or stabilizers are high molecular weight hindered phenols and multifunctional phenols, such as sulfur and phosphorous-containing phenols.

Representative hindered phenols include: 1,3,5-trimethyl 2,4,6-tris (3,5-di-tert-butyl-4-hydroxy-benzyl)benzene; pentaerythritol tetrakis-3(3,5-di-tert-butyl-4-hydroxyphenyl)-propionate; n-octadecyl-3,5-di-tert-butyl-4-hydroxyphenol)-propionate; 4,4'-methylenebis (2,6-tert-butylphenol); 4,4'-thiobis (6-tert-butyl-o-cresol); 2,6-di-tertbutylphenol; 6-(4-hydroxyphenoxy)-2,4-bis(n-octyl-thio)-1,3,5-triazine; di-n-octadecyl 3,5-di-tert-butyl-4-hydroxybenzyl-phosphonate; 2-(n-octylthio)-ethyl 3,5-di-tert-butyl-4-hydroxy-benzoate; and sorbitol hexa[3-(3,5-di-tert-butyl-4-hydroxyphenyl)-propionate].

The adhesive composition can also include other additives including, e.g., fillers, pigments, flow modifiers, dyestuffs, etc., which may be incorporated in minor or larger amounts into the adhesive formulation, depending on the purpose.

These hot melt adhesives may be prepared using techniques known in the art. Typically, the adhesive compositions are prepared by kneading the components in a high shear mixer at an elevated temperature, e.g., about 100° C. to 200° C., until a homogeneous blend is obtained, approximately two hours. Various methods of blending are known and can be used. One useful method uses conventional thermoplastic polymer processing equipment capable of providing sufficiently high shear to intimately blend the high molecular weight polymers and the low molecular weight adhesive components such as tackifying resins, oils or other low molecular weight polymeric materials or blends thereof. Examples of such equipment include single or twin screw extruders, intensive internal mixers, Mixturders, and Sigma Blade mixers, which may be heated to a sufficient processing temperature, typically between 121° C.–177° C. Preferably the blending method provides a homogeneous blend. The resulting adhesives preferably have a viscosity of no greater than about 50,000 cPs at an application temperature of no greater than about 350° F. (177° C.). The viscosity as used herein is a Brookfield viscosity measured using a Brookfield viscometer model No. DV-II with spindle No. 27 at 10 rpm.

The adhesive composition is useful in a variety of applications including, e.g., adhesive fibers, in construction adhesive applications, e.g., on or in nonwoven substrates, e.g., diapers, sanitary napkins, bed pads, and adult incontinence articles. The adhesive composition can be melt blown to produce adhesive fibers. The adhesive product can also be applied to a variety of substrates including, e.g., nonwoven articles, including tissue, using a variety of techniques including, e.g., coating, spraying, laminating, and combinations thereof. Preferably the adhesive composition is applied in an amount sufficient to cause the article to adhere to another substrate, such as tissue, nonwoven, or other conventionally employed substrates, such as polyolefin films.

An increase in surface tension results in improved wettability of the adhesive surface. The increase in surface tension of the adhesive composition is preferably balanced with the surface tension of the substrate to be bonded. It may be advantageous to raise the surface tension of the substrate being bonded, particularly in the case of polyethylene films via film treatment, in order to simultaneously maximize the wettability of the hot melt adhesive composition and the bond performance.

The invention will now be described by way of the following examples. The amounts indicated are in % by weight unless specified differently.

EXAMPLES

Test Procedures

Test procedures used in the examples include the following.

PAFT & SAFT

The peel adhesion failure temperature (PAFT) and shear adhesion failure temperature (SAFT) are determined as follows. An adhesive composition is coated onto Kraft paper by hand using glass rods or shims. The resultant coating is a 1 inch (2.5 cm) wide band that is about 8–10 mils or 0.008 to 0.010 inches 0.2 to 0.25 mm thick. The sample is then conditioned at room temperature for at least 16 hours. The samples are then placed in a programmed oven (Thermatron OV-6) and a 100 gram weight is clamped to a sample in the peel mode to test the PAFT and a 500 gram weight is clamped to a sample in the shear mode to test SAFT. The oven temperature is then increased from 25° C. to 175° C. at a rate of 25° C./hour. When the weight falls off of the sample, the sample is determined to have failed and the oven automatically records the temperature at which the sample fails. The reported result is the average failure temperature of from four to five samples.

Melt Viscosity

Melt viscosity is determined in accordance with the following procedure using a Brookfield Laboratories DVII+ Viscometer in disposable aluminum sample chambers. The spindle used is a SC-31 hot-melt spindle, suitable for measuring viscosity in the range of from 10 to 100,000 centipoise. A cutting blade is employed to cut samples into pieces small enough to fit into the 1 inch (2.5 cm) wide and 5 inches (13 cm) long sample chamber. The sample is placed in the chamber, which is in turn inserted into a Brookfield Thermosel and locked into place with bent needle-nose pliers. The sample chamber has a notch on the bottom that fits the bottom of the Brookfield Thermosel to ensure that the chamber is not allowed to turn when the spindle is inserted and spinning. The sample is heated to 350° F. (177° C.), with additional sample being added until the melted sample is about 1 inch (2.5 cm) below the top of the sample chamber. The viscometer apparatus is lowered and the spindle submerged into the sample chamber.

Lowering is continued until brackets on the viscometer align on the Thermosel. The viscometer is turned on and set to a shear rate that leads to a torque reading in the range of 30 to 60 percent. Readings are taken every minute for about 15 minutes, or until the values stabilize at which time a final reading is taken and recorded.

Surface Tension

Surface tension of a film of adhesive is determined using a set of dyne level marking pens, e.g., Accu Dyne Test™ (Diversified Enterprises). Each pen corresponds to a certain surface tension dyne level. The adhesive composition to be tested is drawn down into a film on a MYLAR film using a draw down square or Bird applicator. Various dyne levels are tested by drawing a line on the film and observing the behavior of the fluid dispensed from the pen. A dyne fluid beads up when the film has a lower surface tension that the fluid. The dyne fluid remains a film when the surface tension of the film is equal to or higher than the surface tension of the fluid.

A result of "ok" indicates that the adhesive composition remained a film without beading up. A result of "-" indicates that the adhesive composition beaded up.

Contact Angle

The contact angle is measured with the use of a goniometer, which has a microsyringe for dispensing accurate droplet sizes and a camera for photographing the angle of the liquid drop as it meets the surface of a film. The contact angle is measured as the angle between the film and the tangent of the liquid drop (i.e., at the interface between the fluid and the film) using analytical fluids such as Diiodomethane and water. The lower the angle, the more effective the coating is in transmitting (i.e., wicking) the liquid through the discontinuous adhesive layer.

Comparative Example A

A hot melt adhesive composition was prepared by combining the following ingredients.

| Wt-% | Ingredient | Generic Description |
| --- | --- | --- |
| 8.9 | Epolene N-15 | propylene homopolymer |
| 0.5 | Irganox 1010 | hindered phenol antioxidant |
| 25.25 | Eastotac H-130R | aliphatic tackifying resin (Eastman, Kingsport, TN) |
| 64.35 | Rextac RT 2280 | low ethylene-propylene copolymer APAO |

The PAFT, SAFT, softening point, and viscosity at 350° C. and 400° C. of the adhesive composition were determined. The results are reported below

| Physical Properties | |
| --- | --- |
| Programmed 100 gramoven peel (PAFT) | 106 |
| Programmed oven shear (SAFT) | 210 |
| Mettler soft point (ASTM D3461) | 306 |
| Viscosity @ 350° F.(177° C.) | 5,200 |
| Viscosity @ 400° F.(204° C.) | 2,500 |

Examples 1A, 1B, & 1C

Atmer 685 surfactant was then added to the adhesive composition of Comparative Example A as follows: 1% Atmer 685 surfactant (Example 1A), 2% Atmer 685 surfactant (Example 1B), and 3% Atmer 685 surfactant (Example 1C). The surface tension of Comparative Example A and Examples 1A–C was then determined. The results are reported in Table 1.

TABLE 1

| % Atmer 685 | Surface Tension Readings (dynes/cm$^2$) | | | | | | | Bond to Water | Mylar |
| --- | --- | --- | --- | --- | --- | --- | --- | --- | --- |
| | 30 | 32 | 34 | 36 | 38 | 40 | 42 | | |
| Comparative Example A | ok | <1 sec | no | — | — | — | — | Beads up | Sticky |
| Example 1A- 1% | ok | ok | ok | ok | 3–5 sec | 1 sec | no | Pretty good | easy peel |
| Example 1B- 2% | ok | ok | <1 sec | No | — | — | — | Good >1% | easy peel |
| Example 1C- 3% | ok | ok | 3–5 sec | <1 sec | no | — | — | ~2% | easy peel |

Comparative Example A has a surface tension of 30–32 dynes and beads up, indicative of a high contact angle (i.e., greater than 90°). The addition of 1 wt-% of nonionic surfactant increases the surface tension to 36–38 dynes and reduces the contact angle to less than 90°. With the addition of 2 wt-% and 3 wt-% the contact angle is further reduced, meaning the adhesive beaded up even less, exhibiting improved fluid spreading tendencies.

Comparative B

An adhesive composition was prepared by combining the following ingredients.

| Wt % | Ingredient | Generic Description |
|---|---|---|
| 19.4 | Europrene Sol T 190 | 15% styrene, linear SIS block copolymer (EniChem, Houston, TX) |
| 0.49 | Irganox 1076 | hindered phenol antioxidant |
| 29.1 | Regalrez 1094 | aliphatic tackifying resin |
| 29.1 | Zonatac 105LT | styrenated terpene tackifying resin |
| 18.9 | Benzoflex 352 | cyclohexane dimethanol dibenzoate solid plasticizer (Velsicol) |

The PAFT, SAFT, softening point, and viscosity at 250° C., 275° C., 300° C. and 325° C. of the adhesive composition were determined. The results are reported below

| Physical Properties | |
|---|---|
| Programmed 100 gram oven peel | 134 |
| Programmed oven shear | 147 |
| Mettler soft. point (ASTM D3461) | 194 |
| Viscosity @ 250° F. (121° C.) | 16,250 cPs |
| Viscosity @ 275° F. (135° C.) | 8,750 |
| Viscosity @ 300° F. (149° C.) | 5,000 |
| Viscosity @ 325° F. (163° C.) | 3,100 |

Examples 2A and 2B

Atmer 685 surfactant was then added to the adhesive composition of Comparative Example B as follows: 0% Atmer 685 surfactant (Comparative Example B), 1.4% Atmer 685 surfactant (Example 2A), and 2.4% Atmer 685 surfactant (Example 2B). The surface tension of Comparative Example A and Examples 2A–B was then determined after initially and then after 2 days and 10 days. The results are reported in Tables 2A–C, respectively.

The delayed crystallization of the Benzoflex 352 affects the surfactant blooming.

TABLE 2A

Day 1

| % Atmer 685 | Dyne Stick Readings (Dynes/cm$^2$) | | | | | | Bond to Water | Mylar |
|---|---|---|---|---|---|---|---|---|
| | 30 | 32 | 34 | 36 | 38 | 40 | | |
| Comparative Example B | ok | ok | ok | 1 sec | No | — | Modest wetting | Easy peel |
| Example 2A- 1.4% | ok | No | — | — | — | — | Beads up | Easy peel |
| Example 2B- 2.4% | ok | no | — | — | — | — | Beads up | Easy peel |

TABLE 2B

Day 2

| % Atmer 685 | Dyne Stick Readings (Dynes/cm$^2$) | | | | | | Bond to Water | Mylar |
|---|---|---|---|---|---|---|---|---|
| | 30 | 32 | 34 | 36 | 38 | 40 | | |
| Comparative Example B | ok | ok | ok | 1 sec | No | — | Modest wetting | Easy peel |
| 2A- 1.4% | ok | ok | ok | ok | 5–15 sec | 2–5 sec | Modest wetting | Easy peel |
| 2B- 2.4% | ok | ok | ok | ok | <1 sec | <1 sec | Modest wetting | Easy peel |

TABLE 2C

Day 10

| % Atmer 685 | Dyne Stick Readings (Dynes/cm$^2$) | | | | | | Bond to Water | Mylar |
|---|---|---|---|---|---|---|---|---|
| | 30 | 32 | 34 | 36 | 38 | 40 | | |
| Comparative Example B | ok | ok | ok | 1 sec | no | — | Modest wetting | Easy peel |
| Example 2A- 1.4% | ok | ok | ok | ok | 5–15 sec | 2–5 sec | Modest wetting | Easy peel |
| Example 2B- 2.4% | ok | ok | ok | ok | <1 sec | <1 sec | Modest wetting | Easy peel |

Example 3

An adhesive composition was prepared by combining the following ingredients.

| Wt % | Ingredient | Generic Description |
|---|---|---|
| 21.75 | XR-5100 Resin | tackifying resin |
| 21.75 | Zonatac 105LT | styrenated terpene tackifying resin |
| 0.5 | Irganox 1076 | hindered phenol antioxidant |
| 44.4 | EVA | (28% vinyl acetate-400 melt index) copolymer |
| 2.4 | Paraffin 140° F. (60° C.) | Wax |
| 2.4 | 195° F. (91° C.) | Microcrystalline Wax |
| 4.8 | Emerest 2400 | Octadecanoic Acid, Monoester with 1,2,3,-Propanetriol; Glyceryl Monostearate |

The viscosity at 250° C., 275° C., 300° C., 325° C. and 350° C. of the adhesive composition was determined. The results are reported below

| Physical Properties | |
|---|---|
| Viscosity @ 250° F. (121° C.) | 12,300 |
| Viscosity @ 275° F. (135° C.) | 6,900 |
| Viscosity @ 300° F. (149° C.) | 4,100 |
| Viscosity @ 325° F. (163° C.) | 2,610 |
| Viscosity @ 350° F. (177° C.) | 1,910 |

Example 4

An adhesive composition was prepared by combining the following ingredients.

| pph | Ingredient | Generic Description |
|---|---|---|
| 16.5 | Vector 4114-D | SIS Block Copolymer |
| 11.9 | 500 Processing Oil | |
| 0.5 | Irganox 1010 | hindered phenol antioxidant |
| 0.5 | Irganox 1076 | hindered phenol antioxidant |
| 46.65 | Escorez 5600 Resin | aromatic dicyclopentadiene resin |
| 13.8 | Benzoflex 352 | cyclohexane dimethanol dibenzoate solid plasticizer (Velsicol) |
| 7.9 | Emerest 2400 | Octadecanoic Acid, Monoester with 1,2,3,-Propanetriol; Glyceryl Monostearate |

The viscosity at 200° C., 250° C., 275° C., 300° C., 325° C. and 350° C. of the adhesive composition was determined.

The results are reported below.

| Physical Properties | |
|---|---|
| Viscosity @ 200° F. (93° C.) | 15,475 |
| Viscosity @ 225° F. (107° C.) | 6,750 |
| Viscosity @ 250° F. (121° C.) | 3,575 |
| Viscosity @ 275° F. (135° C.) | 2,210 |
| Viscosity @ 300° F. (149° C.) | 1,375 |
| Viscosity @ 325° F. (163° C.) | 975 |
| Viscosity @ 350° F. (177° C.) | 1,910 |

Example 5

An adhesive composition was prepared by combining the following ingredients.

| Wt % | Ingredient | Generic Description |
|---|---|---|
| 30.3 | EVA copolymer | (33% vinyl acetate-44 melt index) |
| 0.2 | Irganox 1076 | hindered phenol antioxidant |
| 25.8 | Escorez 2596 | C5 aliphatic tackifying resin |
| 25.8 | Zonatac 105LT | styrenated terpene tackifying resin |
| 13.9000 | Victory amber wax | |
| 2.0000 | Atmer 100 | proprietary nonionic surfactant blend |

| Physical Properties | |
|---|---|
| Viscosity @ 275° F. (135° C.) | 12,100 |
| Viscosity @ 300° F. (149° C.) | 6,800 |
| Viscosity @ 325° F. (163° C.) | 4,190 |
| Viscosity @ 350° F. (177° C.) | 2,740 |
| Viscosity @ 375° F. (191° C.) | 1,850 |

Other embodiments are within the claims.

What is claimed is:

1. An adhesive composition comprising:
   a block copolymer comprising monomers selected from the group consisting of styrene, isoprene, butadiene, and combinations thereof;
   from about 0.5% to about 10% by weight surfactant; and
   a tackifying agent,
   said adhesive composition having a surface tension of at least about 34 dynes/cm$^2$.

2. The composition of claim 1, wherein the block copolymer comprises styrene-isoprene-styrene.

3. The composition of claim 1, wherein said surfactant is nonionic.

4. The composition of claim 1, wherein said surfactant is selected from the group consisting of fatty acid esters.

5. The composition of claim 1, wherein the surfactant comprises glycerol monostearate.

6. The composition of claim 2, wherein the surfactant comprises glycerol monostearate.

7. The composition of claim 1 comprising:
   from about 10 to about 80% by weight of said polymer,
   from about 0.5 to about 10% by weight of said surfactant, and
   from about 20 to about 50% by weight tackifying agent.

8. The composition of claim 1 further comprising a plasticizer.

9. The composition of claim 8, wherein said plasticizer comprises a crystallizing plasticizer.

10. The composition of claim 7, further comprising a crystallizing plasticizer.

11. An article comprising:
    a nonwoven substrate; and
    an adhesive composition disposed on said substrate,
    said adhesive composition having a surface tension of at least about 34 dynes/cm$^2$.

12. The article of claim 11, wherein said substrate is selected from the group consisting of a diaper, a sanitary napkin, a bed pad, and an adult incontinence article.

13. An article comprising:
    adhesive fibers comprising an adhesive composition comprising a block copolymer comprising monomers selected from the group consisting of styrene, isoprene, butadiene, and combinations thereof;
    from about 0.5% to about 10% by weight surfactant; and
    a tackifying agent,
    said adhesive composition having a surface tension of at least about 34 dynes/cm$^2$.

* * * * *